US009394332B2

(12) United States Patent
Markert-Hahn et al.

(10) Patent No.: US 9,394,332 B2
(45) Date of Patent: *Jul. 19, 2016

(54) METHOD FOR BISULFITE TREATMENT

(75) Inventors: Christine Markert-Hahn, Penzberg (DE); Dirk Block, Bichl (DE)

(73) Assignee: Epigenomics AG, Berlin (DE)

( * ) Notice: Subject to any disclaimer, the term of this patent is extended or adjusted under 35 U.S.C. 154(b) by 1002 days.

This patent is subject to a terminal disclaimer.

(21) Appl. No.: 10/647,720

(22) Filed: Aug. 25, 2003

(65) Prior Publication Data

US 2004/0241704 A1   Dec. 2, 2004

(51) Int. Cl.
C12Q 1/68 (2006.01)
C12P 19/34 (2006.01)
C07H 19/00 (2006.01)
C07H 21/00 (2006.01)

(52) U.S. Cl.
CPC .............. *C07H 21/00* (2013.01); *C12Q 1/6827* (2013.01); *C12Q 1/6834* (2013.01)

(58) Field of Classification Search
USPC ................ 435/6, 91.2, 6.12; 536/22.1, 24.31, 536/24.33
See application file for complete search history.

(56) References Cited

U.S. PATENT DOCUMENTS

| 4,683,202 | A | 7/1987 | Mullis ............................. 435/91 |
| 5,130,238 | A | 7/1992 | Malek et al. .................... 435/91 |
| 5,137,806 | A | 8/1992 | LeMaistre et al. ................ 435/6 |
| 5,210,015 | A | 5/1993 | Gelfand et al. ................... 435/6 |
| 5,234,809 | A | 8/1993 | Boom et al. .................... 435/91 |
| 5,487,972 | A | 1/1996 | Gelfand et al. ................... 435/6 |
| 5,552,277 | A | 9/1996 | Nelson et al. .................... 435/6 |
| 5,595,890 | A | 1/1997 | Newton et al. ............... 435/91.2 |
| 5,639,611 | A | 6/1997 | Wallace et al. .................... 435/6 |
| 5,786,146 | A | 7/1998 | Herman et al. .................... 435/6 |
| 5,804,375 | A | 9/1998 | Gelfand et al. ................... 435/6 |
| 6,174,670 | B1 | 1/2001 | Wittwer et al. ................... 435/6 |
| 6,291,166 | B1* | 9/2001 | Gerdes et al. .................... 435/6 |
| 6,297,017 | B1* | 10/2001 | Schmidt et al. ............. 435/6.18 |
| 6,331,393 | B1 | 12/2001 | Laird et al. ....................... 435/6 |
| 8,137,937 | B2* | 3/2012 | Markert-Hahn ............. 435/91.2 |
| 2003/0096273 | A1* | 5/2003 | Gagna ............................... 435/6 |
| 2003/0152950 | A1 | 8/2003 | Garner et al. |

FOREIGN PATENT DOCUMENTS

| EP | 0 201 184 B1 | 12/1992 |
| EP | 0 200 362 B1 | 1/1993 |
| EP | 0 389 063 B1 | 8/1997 |
| JP | 06-217775 | 8/1994 |
| JP | 07-177886 | 7/1995 |
| JP | 07-177887 | 7/1995 |
| WO | WO 90/01069 | 2/1990 |
| WO | WO 90/06045 | 6/1990 |
| WO | WO 92/02638 | 2/1992 |
| WO | WO 96/41811 | 12/1996 |
| WO | WO 99/16781 | 4/1999 |
| WO | WO 99/40098 | 8/1999 |
| WO | WO 00/32762 | 6/2000 |
| WO | WO 00/34463 | 6/2000 |
| WO | WO 01/09389 A2 | 2/2001 |
| WO | WO 01/37291 A1 | 5/2001 |
| WO | WO 01/40459 A2 | 6/2001 |
| WO | WO 01/98528 A3 | 12/2001 |
| WO | WO 02/31186 A2 | 4/2002 |
| WO | WO 03/038121 A2 | 5/2003 |

OTHER PUBLICATIONS

Herman, J., et al., "Methylation-specific PCR: a Novel PCR Assay for Methylation Status of CpG Islands," *Proc. Natl. Acad. Sci. U S A*. 93(18):9821-6, Sep. 3, 1996.
Abramson, R., et al., 1993, "Nucleic Acid Amplification Technologies", *Curr Opinion Biotechnology*, 4:41-47.
Alderton, R., et al., 1992, "Magnetic Bead Purification of M13 DNA Sequencing Templates", *Analytical Biochemisty*, 201:166-169.
Barany, F., 1991, "Review: The Ligase Chain Reaction in a PCR World", *PCR Methods and Applications*, 1(1):5-16.
Barany, F., 1991, "Genetic Disease Detection and DNA amplification using cloned thermostable ligase", *Proc. Natl. Acad. Sci. USA*, 88:189-193.
Benyajati, C., et al., 1980, "Alcohol dehydrogenase in *Drosophila*: Isolation and characterization of messenger RNA and cDNA clone", *Nucleic Acids Research*, 8(23):5649-5667.
Clark, S., 1994, "High sensitivty mapping of methylated cytosines", *Nucleic Acids Research*, 22(15):2990-2997.
Feil, R., et al., 1994, "Methylation analysis on individual chromosomes: improved protocol for bisulphate genomic sequencing", *Nucleic Acids Research*, 22(4):695-696.
Fraga, M., et al., 2002, "DNA Methylation: A Profile of Methods and Applications", *BioTechniques*, 33(3)632649.
Frommer, M., et al., 1992, "A Genomic sequencing protocol that yields a positive display of 5-methylcytosine residues in individual DNA strands", *Proc. Natl. Acad. Sci. USA*, 89:1827-1831.
Goyon, C., et al, 1994, "Perpetuation of Sytosine Methylation in *Asobolus immerses* implies a Novel Type of Maintenance Methylase", *J. Med. Biol.*, 240:42-51.
Grigg, G., 1996, "Sequencing 5- methylcytosine residues by bisulphate method", *DNA Sequence*, 6:189-198.
Grigg, G., et al., 1994, "Sequencing 5- methylcytosine residues in Genomic DNA", *BioEssays*, 16(6):431-436.
Grunau, C., et al., 2001,."Bisulfite genomic sequencing: systematic investigation of critical experimental parameters", *Nucleic Acids Research*, 29(13):e65-5.

(Continued)

*Primary Examiner* — Kenneth R. Horlick
*Assistant Examiner* — Joyce Tung
(74) *Attorney, Agent, or Firm* — Lathrop & Gage LLP; James H. Velema, Esq.

(57) ABSTRACT

The present application is directed to a method for performing a bisulfite reaction to determine methylation positions in a nucleic acid, i.e. methylated and non-methylated cytosines, whereby the nucleic acid is bound to a solid phase during the deamination and/or desulfonation step of the bisulfite reaction. The solid phase is preferably a material comprising glass or silica, more preferably a glass fleece, glass membrane or a magnetic glass particle. Further, the use of a solid phase for binding a nucleic acid during the deamination and/or desulfonation step of the bisulfite reaction is disclosed and a kit containing a bisulfite reagent and a solid phase.

11 Claims, 1 Drawing Sheet

(56) References Cited

OTHER PUBLICATIONS

Guatelli, J., et al., 1990, "Isothermal, in vitro amplification of nucleic acids by a multienzyme reaction modeled after retroviral replication", *Proc. Natl., Acad, Sci. USA*. 87:1874-1878.

Intergen Company, "CpGenome™ DNA Modification Kit", Catalog No: S7820, 2003.

Intergen Company, "Methylation Specific PCR" Literature, 2003.

Jakobi, R., et al., 1988, "Filter-Supported Preparation of λ Phage DNA", *Analytical Biochemistry*, 175:196-201.

Kwoh, D., et al., 1989, "Transcription-based amplification system and detection of amplified human immunodeficiency virus type 1 with a bead-based sandwich hybridization format", *Proc. Natl. Acad. Sci. USA*, 86:1173-1177.

Komlyama, M., et al., 1994, "Catalysis of Diethylenetriamine for Bisulfite-Induced Deamination of Cytosine in Oligodeoxyribonucleotides", *Tetrahedron Letters*, 35(44):8185-8188.

Marko, M., 1982, "A procedure for the large-scale isolation of Highly purified Plasmid DNA Using Alkaline Extraction and Binding to Glass Powder", *Analytical Biochemistry*, 121:382-387.

Morrow, C., et al., 1989, "Structure of the Human Genomic Glutathione S-transferase-π gene", *Gene*, 75:3-11.

Oakeley, E., 1999, DNA Methylation analysis: a review of current methodologies:, *Pharmacology & Therapeutics*, 84:389-400.

Oakeley, E., et al., 1999, "Changing Functionality of Surface by Directed Self-Assembly Using Oligonucleotides—The Oligo-Tag", *BioTechniques*, 27(4):752-760.

Olek, A., et al., 1996, "A modified and improved method of bisulphate based cytosine Methylation analysis", *Nucleic Acids Research*, 24(24):5064-5066.

Paulin, R., et all., 1998; "Urea improves efficiency of bisulphate-mediated sequencing of 5'-methylcytosine in genomic DNA", *Nucleic Acids Research*, 26(21):5009-5010.

Raizis, A., et al., 1995, "A Bisulfite Method of 5'-methylcytosine that minimizes template Degradation", *Analytical Biochemistry*, 226:161-166.

Volgelstein, B., et al., 1979, "Preparative and analytical purification of DNA from agarose", *Proc. Natl. Acad. Sci. USA*, 76(2):615-619.

Wang, R., et al., 1980, "Comparison of bisulfite modification of 5'-methylcytosine and deoxycytidine residues", *Nucleic Acids Research*, 8(20):4777-4790.

Warnecke, P., et al., 1997, "Detection and measurement of PCR bias in quantitative methylation analysis of bisulphate-treated DNA", *Nucleic Acids Research.*, 25(21):4422-4426.

Warnecke, P., et al., 2002, "Identification and resolution of artifacts in bisulfite sequencing", *Methods*, 27:101-107.

Whelen, C., 1996, "The Role of Nucleic Acid Amplification and Dtection in the Clinical Microbiology Laboratory", *Annu. Rev. Microbiol*, 50:349-373.

Wu, D., et al., 1989, "The Ligation Amplification Reaction (LAR)—Amplification of Specific DNA Sequences Using Sequential Rounds of Template-Dependent Ligation", *Genomic*, 4:560-569.

Hayatsu, Hikoya, et al., "Polynucleotide-Chitosan Complex, an Insoluble but Reactive Form of Polynucleotide[1]," Chem. Pharm. Bull., 45(8), pp. 1363-1368 (1997).

* cited by examiner

METHOD FOR BISULFITE TREATMENT

BACKGROUND OF THE INVENTION

1. Field of the Invention

The present application is directed to a method for performing a bisulfite reaction to determine methylation positions in a nucleic acid, i.e. methylated and non-methylated cytosines, whereby the nucleic acid is bound to a solid phase during the deamination and/or desulfonation step of the bisulfite reaction. The solid phase is preferably a material comprising glass or silica, more preferably a glass fleece, glass membrane or a magnetic glass particle. Further, the use of a solid phase for binding a nucleic acid during the deamination and/or desulfonation step of the bisulfite reaction is disclosed and a kit containing a bisulfite reagent and a solid phase.

Genes constitute only a small proportion of the total mammalian genome, and the precise control of their expression in the presence of an overwhelming background of noncoding desoxyribonucleic acid (DNA) presents a substantial problem for their regulation. Noncoding DNA, containing introns, repetitive elements, and potentially active transposable elements requires effective mechanisms for its long term silencing. Mammals appear to have taken advantage of the possibilities afforded by cytosine methylation to provide a heritable mechanism for altering DNA-protein interactions to assist in such silencing. DNA methylation is essential for the development of mammals; and plays a potential role during aging and cancer. The involvement of methylation in the regulation of gene expression and as an epigenetic modification marking imprinted genes is well established. In mammals, methylation occurs only at cytosine residues and more specifically only on cytosine residues adjacent to a guanosine residue, i.e. at the sequence CG. The detection and mapping of DNA methylation sites are essential steps towards understanding the molecular signals which indicate whether a given sequence is methylated.

2. Description of Related Art

This is currently accomplished by the so-called bisulfite method described by Frommer, M., et al., Proc Natl Acad Sci USA 89 (1992) 1827-31) for the detection of 5-methyl-cytosines. The bisulfite method of mapping 5-methylcytosine uses the effect that sodium hydrogen sulfite reacts with cytosine but not or only poorly with 5-methyl-cytosine. Cytosine reacts with bisulfite to form a sulfonated cytosine reaction intermediate being prone to deamination resulting in a sulfonated uracil which can be desulfonated to uracil under alkaline conditions. It is common knowledge that uracil has the base pairing behavior of thymine different to the educt cytosine whereas 5-methylcytosine has the base pairing behavior of cytosine. This makes the discrimination of methylated or non-methylated cytosines possible by e.g. bisulfite genomic sequencing (Grigg, G. and Clark, S., Bioessays 16 (1994) 431-6; Grigg, G. W., DNA Seq 6 (1996) 189-98) or methylation specific PCR (MSP) disclosed in U.S. Pat. No. 5,786,146.

There are various documents addressing specific aspects of the bisulfite reaction (Benyajati, C., et al., Nucleic Acids Res 8 (1980) 5649-67) make general investigations to the bisulfite modification of 5-methyl-deoxycytosine and deoxycytosine (Olek, A., et al., Nucleic Acids Res 24 (1996) 5064-6) disclose a method for bisulfite base sequencing whereby bisulfite treatment and subsequent PCR steps are performed on material embedded in agarose beads. In the bisulfite method as disclosed by Clark, S. J., et al., Nucleic Acids Res 22 (1994) 2990-7, the sample is desalted after deamination. Raizis, A. M., et al., Anal Biochem 226 (1995) 161-6 disclose a bisulfite method of 5-methylcytosine mapping that minimizes template degradation. They investigate the influence of pH, temperature and time of reaction. Similar investigations have been made by Grunau, C., et al., Nucleic Acids Res 29 (2001) E65-5 or Warnecke, P. M., et al., Methods 27 (2002) 101-7. Different additional components in the bisulfite mixture are disclosed by WO 01/98528 or by Paulin, R., et al., Nucleic Acids Res 26 (1998) 5009-10. An additional bisulfite step after bisulfite treatment and PCR is disclosed in WO 02/31186. Komiyama, M. and Oshima, S., Tetrahedron Letters 35 (1994) 8185-8188) investigate the catalysis of bisulfite-induced deamination of cytosine in oligodeoxyribonucleotides.

Kits for performing bisulfite treatments are commercially available from Intergen, distributed by Serologicals Corporation, Norcross, Ga., USA, e.g. CpGenome™ DNA modification kit.

A variation of the bisulfite genomic sequencing method is disclosed by Feil, R., et al., Nucleic Acids Res 22 (1994) 695-6, whereby the genomic DNA is bound to glass beads after deamination and washed. After elution the nucleic acid is desulfonated. It is known that nucleic acids can be isolated by the use of their binding behavior to glass surfaces, e.g. adsorption to silica gel or diatomic earths, adsorption to magnetic glass particles (MGPs) or organo silane particles under chaotropic conditions. Extraction using solid phases usually contains the steps of adding the solution with the nucleic acids to the solid phase under conditions allowing binding of the substance of interest to the solid phase, removal of the remainder of the solution from the solid phase bound nucleic acids and subsequent release of the nucleic acids from the solid phase into a liquid eluate (sometimes called elution). The result of the such process is usually a solution containing the substance of interest in dissolved state.

SUMMARY OF INVENTION

All prior art methods for the bisulfite treatment have disadvantages. Therefore, the problem to be solved by the present invention was to provide a method which overcomes the disadvantages of the prior art methods.

The problem discussed above is solved by providing a method for the conversion of cytosine bases in a nucleic acid to uracil bases whereby 5-methyl-cytosine bases are not significantly converted ("bisulfite reaction" or "bisulfite treatment") whereby the nucleic acid is bound to a solid phase during the deamination and/or desulfonation step of the bisulfite reaction. Preferably, the solid phase is a glass fleece, a glass membrane or a magnetic glass particle. Further, the present invention discloses uses of a solid phase in the deamination and/or desulfonation step of the bisulfite reaction and kits containing a solid phase and reagents for performing a bisulfite reaction.

The use of a solid phase during the deamination and/or desulfonation step of the bisulfite reaction, preferably in the desulfonation step, has the advantage that the handling is simpler and/or easily amenable to automation. For example, when glass fleeces are used for the deamination and/or desulfonation steps, no time consuming DNA precipitation reactions are necessary; bound-free separation can easily be achieved by centrifugation, the dead volume of glass fleece is neglectable and therefore washing steps are very effective. This is an advantage when the bisulfite treatment DNA is used for PCR where potential inhibitors can reduce the sensitivity significantly. The method according to the invention can be easily performed manually and is therefore well suited for smaller laboratories where routine analysers are not available. For larger laboratories with higher sample throughput, the use a solid phase that can be handled by routine analyzers, in particular magnetic glass particles, is advantageous. In a routine bisulfite reaction denaturing conditions are chosen as bisulfite can only react with pyrimidines that are not involved in base-pairing. Therefore, it is surprising that the bisulfite reaction can be performed successfully in a satisfying manner by the method according to the invention as the nucleic acid is bound to the surface of the solid phase by various interactions possibly influencing the success of the bisulfite reaction.

DETAILED DESCRIPTION OF THE INVENTION

Figure 1:
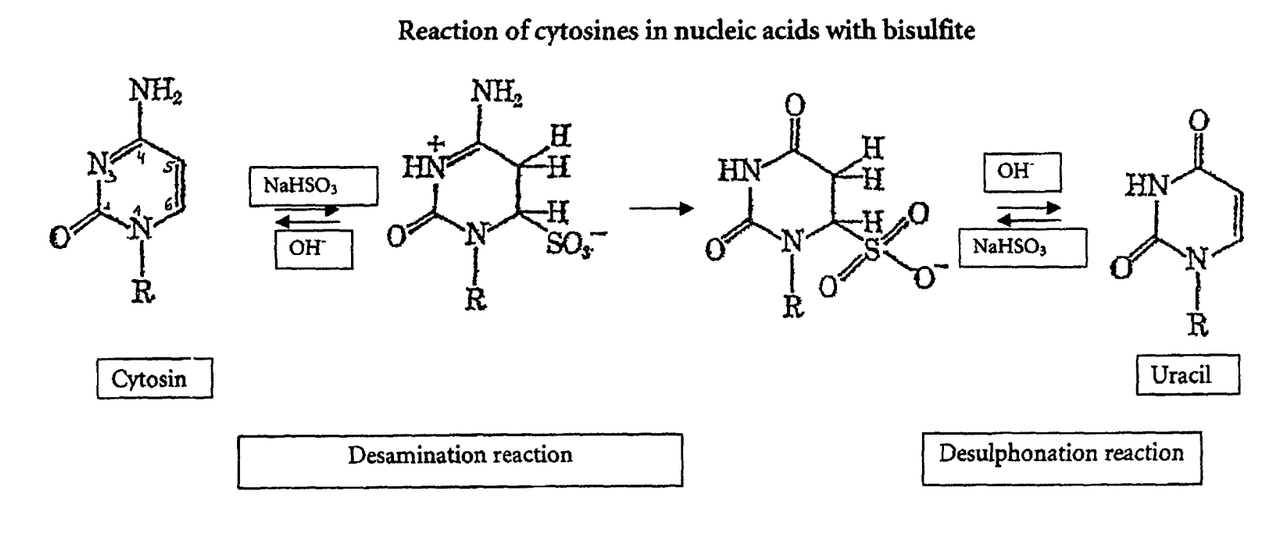
FIG. 1 is a schematic drawing showing the reaction of cytosine with bisulfite according to an embodiment of the invention

According to the invention the term a "bisulfite reaction", "bisulfite treatment" or "bisulfite method" shall mean a reaction for the conversion of cytosine bases in a nucleic acid to uracil bases in the presence of bisulfite ions whereby 5-methyl-cytosine bases are not significantly converted. This reaction for the detection of methylated cytosines is described in detail by Frommer et al., supra and Grigg and Clark, supra. The bisulfite reaction contains a deamination step and a desulfonation step which can be conducted separately or simultaneously (see FIG. 1; Grigg and Clark, supra). The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases (Frommer et al., supra).

The method of the invention can be performed in several arrangements of bisulfite reaction and immobilisation steps. In a first embodiment, the deamination and desulfonation step is made while the nucleic acid is bound to the solid phase. Therefore in a preferred embodiment of the invention, a method for the conversion of cytosine bases in a nucleic acid to uracil bases is disclosed ("bisulfite reaction") whereby 5-methyl-cytosine bases are not significantly converted, comprising the steps of
 a) binding the nucleic acid to a solid phase,
 b) incubating the solid phase bound nucleic acid in the presence of sulfite ions whereby the nucleic acid is deaminated,
 c) optionally washing the deaminated solid phase bound nucleic acid,
 d) incubating the deaminated solid phase bound nucleic acid under alkaline conditions whereby the deaminated nucleic acid is desulfonated,
 e) optionally washing the deaminated and desulfonated solid phase bound nucleic acid, and
 f) optionally eluting the deaminated and desulfonated nucleic acid from the solid phase.

In a second embodiment of the invention, the desulfonation step is made while the nucleic acid is bound to the solid phase. Therefore, in another preferred embodiment of the invention, a method for the conversion of cytosine bases in a nucleic acid to uracil bases is disclosed whereby 5-methyl-cytosine bases are not significantly converted ("bisulfite reaction"), comprising the steps of
 a) incubating the nucleic acid in the presence of sulfite ions whereby the nucleic acid is deaminated,
 b) binding the deaminated nucleic acid to a solid phase,
 c) optionally washing the deaminated solid phase bound nucleic acid,
 d) incubating the deaminated solid phase bound nucleic acid under alkaline conditions whereby the deaminated nucleic acid is desulfonated,
 e) optionally washing the deaminated and desulfonated solid phase bound nucleic acid, and
 f) optionally eluting the deaminated and desulfonated nucleic acid from the solid phase.

In a third embodiment, the deamination step is made while the nucleic acid is bound to the solid phase. Therefore, in another preferred embodiment of the invention, a method for the conversion of cytosine bases in a nucleic acid to uracil bases is disclosed whereby 5-methyl-cytosine bases are not significantly converted ("bisulfite reaction"), comprising the steps of
 a) binding the nucleic acid to a solid phase,
 b) incubating the solid phase bound nucleic acid in the presence of sulfite ions whereby the nucleic acid is deaminated,
 c) optionally washing the solid phase bound nucleic acid,
 d) eluting the deaminated nucleic acid from the solid phase,
 e) incubating the deaminated nucleic acid under alkaline conditions whereby the deaminated nucleic acid is desulfonated.

The expert skilled in the art knows how to perform the bisulfite reaction, e.g. by referring to Frommer et al., supra or Grigg and Clark, supra who disclose the principal parameters of the bisulfite reaction. From Grunau et al., supra, it is known to the expert in the field what variations of the bisulfite method are possible. The influence of incubation time and temperature on deamination efficiency and parameters affecting DNA degradation is disclosed.

In an embodiment of the invention, the nucleic acid is desoxyribonucleic acid (DNA), in particular genomic DNA or nucleic acid, i.e. the DNA or nucleic acid which is found in the organism's genome and is passed on to offspring as information necessary for survival. The phrase is used to distinguish between other types of DNA, such as found within plasmids. The source of the nucleic acid may be eukaryotic or prokarytic, preferably from vertebrates, particularly from mammalians, most preferred from animals or humans.

In an embodiment of the invention, the nucleic acid is bound to the solid phase, which is unmodified, i.e. the nucleic acid is directly bound without any compound mediating the binding to the solid phase. The nucleic acid binds to the unmodified surface of the solid phase, whereby binding to the surface shall also take into account that the solid phase may contain pores and that the nucleic acid may be bound to surfaces in pores of the solid phase. In embodiments according to the invention, the solid phase may be an ion exchanger (commercially available from e.g. Amersham Biosciences Europe, Freiburg, Germany), able to bind a nucleic acid under specific conditions, hydroxylapatite (commercially available from Sigma, Taufkirchen, Germany), glass or silica or materials comprising glass or silica, preferably with an unmodified surface. In another embodiment the solid phase may be modified, i.e. the solid phase indirectly binds the nucleic acid with a compound mediating the binding to the solid phase, e.g. by sequence specific binding of the nucleic acid to oligonucleotides attached to the surface or streptavidin (attached to the surface of the solid phase) binding to biotin-labelled DNA. Suitable particles therefore are commercially available from DYNAL, Oslo, Norway and described e.g. in WO 90/06045. The term "unmodified" shall mean that there is no further chemical modification, i.e. no other chemical groups are attached covalently or non-covalently. The term "unmodified surface", "unmodified silica surface" or "unmodified glass surface" shall mean that no other chemical groups are attached covalently or non-covalently which serve as an intermediary substance for nucleic acid binding and where the nucleic acids bind to the intermediary substance and not to the silica surface itself. Therefore, the nucleic acids bind preferably by hydrogen bonding and other atomic forces directly to the "unmodified surface". An example of a modified surface are silica surfaces to which oligonucleotides are attached which bind in sequence-specific manner nucleic acid molecules. Another example for modified silica surfaces are silica surfaces coated with streptavidin which binds to biotinylated DNA molecules.

In a particularly preferred embodiment according to the invention the solid phase is a material comprising glass or silica, preferably with an unmodified (glass or silica) surface, e.g. glass fibers or, diatomaceous earth, glass beads or particles, glass membranes or magnetic glass particles or other substances covered with an unmodified glass surface. Particularly preferred are glass fleeces or glass membranes or magnetic glass particles. Such solid phases are disclosed e.g. in EP 0 389 063 or U.S. Pat. No. 5,234,809.

The conditions for binding DNA or nucleic acids to glass or silica surfaces are basically known to the expert in the field. These processes are described in detail by various documents. In Vogelstein, B. and Gillespie, D., Proc Natl Acad Sci USA 76 (1979) 615-9, for instance, a procedure for binding nucleic acids from agarose gels in the presence of sodium iodide to ground flint glass is proposed. The purification of plasmid DNA from bacteria on glass dust in the presence of sodium perchlorate is described in Marko, M. A., et al., Anal Biochem 121 (1982) 382-7. In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi, R., et al., Anal Biochem 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. In a preferred embodiment of the invention, magnetic glass particles are used to bind the nucleic acids after precipitation by adding salt and ethanol as described e.g. in Alderton, R. P., et al., Anal Biochem 201 (1992) 166-9 and PCT GB 91/00212.

In a very preferred embodiment of the invention, the solid phase is a magnetic glass particle, preferably with an unmodified glass surface. The magnetic glass particles are a solid dispersion of small magnetic cores in glass, i.e. they are glass droplets in which very small magnetic objects are dispersed. Those objects that are referred to as magnetic are drawn to a magnet, i.e. ferr- or ferromagnetic or superparamagnetic materials for instance. Paramagnetic substances are not useful as they are only drawn to a magnetic very weakly which is not sufficient for a method according to this invention. Preferred are ferr- or ferromagnetic materials, in particular if they have not yet been premagnetized. Premagnetization in this context is understood to mean bringing in contact with a magnet, which increases the remanence. Preferred magnetic materials are iron or iron oxide as e.g. magnetite ($Fe_3O_4$) or $Fe_2O_3$, preferably $\gamma$-$Fe_2O_3$. In principle, barium ferrite, nickel, cobalt, Al—Ni—Fe—Co alloys or other ferr- or ferromagnetic material could be used. Particularly preferred according to the present invention are the magnetic glass particles described in WO 96/41811, WO 00/32762 and WO 01/37291.

In a very preferred embodiment of the invention, the magnetic glass particles have a tow iron leach, as iron is an inhibitor of the subsequent amplification reaction, i.e. iron is an enzymatic inhibitor. Therefore, this is an important feature of the magnetic glass particles. Preferably, the iron leach in water or 1 M HCl (for 20 min) is below 40 ppm, more preferably below 20 ppm, most preferred below 10 ppm. In the most preferred embodiment of the invention, the magnetic glass particles are those described in the international application WO 01/37291 which are also publicly available in the MagNA Pure LC DNA Isolation Kit I (Roche, Mannheim, Germany). These particles sediment slowly and can therefore be advantageously used in an automated method according to the invention. The production thereof is summarized below.

The magnetic glass particles are substantially spherical and have a small diameter and contain at least one magnetic object with a diameter between 5 and 500 nm. This has surprising consequences on the sedimentation kinetics, quantified by the half time values $t_{1/2}$, which is the time span until 50% of the particles have sedimented from a specific volume element. The half-life period for the sedimentation of a 3 mg/ml weight-per-volume suspension of the MGPs with an unmodified glass surface according to the invention in isopropanol is more than 3 min, preferably 4 min, more preferably 6 min. However the most preferred values for the half-life period is more than 10 min or even more than 20 min. The magnetic objects of the most preferred MGPs may be e.g. a magnetic pigment. The size of the magnetic objects is in the nanoscale range, i.e. between 5 to 500 nm, preferably between 10 to 200 nm, most preferably between 15 to 50 nm. Suitable magnetic pigments are manufactured by the company CERAC which have a mean diameter of 23 nm and consist of $\gamma$-$Fe_2O_3$ (BET-surface 50 $m^2$/g, CERAC: P.O. Box 1178, Milwaukee, Wis. 53201-1178 USA; Article-No. 1-2012). The most preferred magnetic glass particles according to the present invention are further characterized by the fact that the MGPs have a particle diameter between 0.5 µm and 5 µm, preferably between 1 µm to 2 µm as determined by high resolution scanning electron microscopy, whereas the magnetic objects have a diameter between 5 to 500 nm, preferably between 10 to 200 nm, most preferably in the range of 15 to 50 nm as described above. Hence, the MGPs are further characterized by a diameter ratio of magnetic pigment core to magnetic glass particle of less than 1 to 10 as determined by high resolution scanning electron microscopy. The most preferred MGPs are microporous but have a highly-structured and therefore relatively large surface with more than 6 $m^2$/g. Preferably, the magnetic glass particles have a surface area in the range of 5 to 100 $m^2$/g, preferably 5 to 90 $m^2$/g, more preferably in the range of 10 to 50 $m^2$/g, most preferably in the range of 15 to 30 $m^2$/g. This can be determined by the Braunauer-Emett-Teller-method using an automated commercial apparatus. For a discussion of this method, familiarly called the BET method, see Braunauer, in "The Adsorption of Gases and Vapors" (1943), Princeton University Press.

The magnetic glass particles used in the present invention may be provided in different formulations essentially as described in WO 01/37291. It is possible to provide them in the form of a tablet, as a powder or preferably as a suspension. In a preferred embodiment of the invention these suspensions contain between 5 to 60 mg/ml magnetic glass particles (MGPs). In another embodiment of the invention the silica-containing material is suspended in aqueous buffered solutions which may optionally contain a chaotropic agent in a concentration of between 2 and 8 mol/l, and preferably between 4 and 6 mol/l. Chaotropic salts are sodium iodide, sodium perchlorate, guanidinium thiocyanate, guanidinium isothiocyanate or guanidinium hydrochloride. A chaotropic agent according to the present invention is any chemical substance which will disturb the ordered structure of liquid water and will have the effect that DNA or RNA will bind to the MGPs according to the present invention if this agent is present in the DNA or RNA containing solution. Other compounds known to the expert in the field are also possible.

In a preferred embodiment of the invention, the magnetic glass particles are manufactured by the sol-gel method described in WO 01/37291, WO 00/37291 and WO 96/41811, in particular wherein the sol-gel method comprises the steps of:
suspending magnetic objects in a sol
hydrolyzing the sol to cover the magnetic objects with a gel
spray-drying the magnetic objects covered with a gel in a two-nozzle spray-drier, and
sintering the spray-dried powder to form a glass from the gel covering the magnetic objects.

Preferred MGPs according to the invention are magnetic glass particles manufacture according to example 8 of WO 00/32762 containing microna mat black as the magnetic pigment. The most preferred MGPs according to the invention are manufactured according to the international application WO 01/37291 which are also provided in the MagNA Pure LC DNA Isolation Kit I (Roche, Mannheim, Germany)). They are also produced by the sol-gel-method as described in the international application WO 01/37291 using magnetic objects or pigments with a diameter of about 23 nm (manufactured by CERAC consisting of $\gamma$-$Fe_2O_3$; CERAC: P.O. Box 1178, Milwaukee, Wis. 53201-1178 USA; Artide-No. I-2012). After the magnetic objets are covered with a gel, a powder is created by spraying the slurry through a two-fluid nozzle. Suitable spray-drying systems are produced by Nubilosa Molekularzerstäubung, Ladisch GmBH & Co. KG, Konstanz, Germany, e.g. the "Labor-Zerstäubungstrockner (Typ LTK)" or by Büchi AG, Uster, Switzerland, e.g. the Mini Spray Dryer (Type B-191). Because of the diameter ratios of magnetic cores to the glass shell are less than 1 to 10, preferably between 1:10 and 1:1000, the geometry and the number of incorporated magnetic cores or of their inert carriers do not determine shape and size of the particles but the conditions of manufacturing, in particular the conditions during spray drying. In other words, the choice of pressure, inlet temperature, outlet temperature and flow rate during the spray drying procedure are the degrees of freedom which determines the size distribution, the shape of the glass drops and thereby will modify the MGPs. Therefore, the nozzles of the spray-drying system are heated. The inlet temperature is between 120° C. and 500° C., preferably between 170° C. and 230° C. or 150° C. and 230° C., most preferably between 150° C. and 200° C. or 190° C. and 210° C. or at 200° C. or slightly less. The outlet temperature depends on the boiling point of the sol and thereby on the solvent and may be above, equal or slightly under, i.e. less than 10° C., the boiling point of the solvent. When ethanol is used as solvent, it is between 50° C. and 300° C., preferably 70° C. and 150° C., most preferably between 80° C. and 110° C. The optimal temperature is between 90° C. to 100° C. The nozzle pressure is more than 3 bar, preferably it is regulated to 4 to 6 bar. The artisan will appreciate the fact that the exact parameters will depend on the spray-drying system used. However, he can transfer the teachings of the present invention to any other spray-drying system and find out the parameters by taking the disclosures of this invention into account. Formulas as described in Masters: "Spray Drying Handbook" (1991), John Wiley & Sons, New York can lead him the way to find out which parameters have to be chosen for another setting. Preferably, he will question the manuals of his spray-drying system or contact the technical service of the spray-drying system manufacturer. To optimize the yield, the densification or sinter temperature should be as high as possible, i.e. slightly below the melting range. The exact temperatures depend on the glass composition but may be between 400° C. to 1200° C. In the case of the EJ glass composition described in WO 01/37291 the sinter temperature is between 720° C. and 770° C., preferably around 750° C. It is in the skill of the artisan to find out the temperatures for each glass composition when taking the teachings of the present invention into account. Afterwards, the powder is heated for 1 hour to 200° C., optionally cooled to room temperature and heated to 750° C. (densification or sinter temperature) in a nitrogen atmosphere with a heating rate of 1 K/min and is held at that temperature for 1 hour. Then the furnace is cooled to 150° C. and heated again to 200° C. for one hour in air. After the cooling to room temperature, the powder is transferred to a sieve (50 μm) and sieved for 30 min. The sieved sample is bottled and sterilized at 200° C. for 4 h and then cooled to 80° C. Then the glass vessels are taken from the oven, covered with sterile foil and closed.

The experimental procedure for binding the nucleic acid to unmodified glass or silica surfaces (of preferably the magnetic glass particles) can be described in detail as follows. It is preferably performed in the presence of chaotropic salts with a concentration of between 1 and 8 mol/l, and preferably between 2 and 6 mol/l. Chaotropic salts can be sodium iodide, sodium perchlorate, guanidinium thiocyanate, guanidinium isothiocyanate or guanidinium hydrochloride. A chaotropic agent according to the present invention is any chemical substance which disturbs the ordered structure of liquid water and has the effect that DNA (or RNA) binds to the magnetic glass particles if this agent is present in the DNA (or RNA) containing solution. Other biological substances known to the expert in the field may also be present. Still other substances are also possible. To bind the mixture of nucleic acids and optionally other biological compounds, the glass beads with an unmodified glass surface are added to the mixture and incubated for a period of time sufficient for the binding to occur. Experts are usually familiar with the duration of the incubation step. This step can be optimized by determining the quantity of immobilized nucleic acids on the surface at different points in time. Incubation times of between 10 seconds and 30 minutes can be appropriate for nucleic acids. Then the reagents for performing the different steps of the bisulfite reaction are added (or may even have been present before). After incubation or washing, the nucleic acids may separated from the liquid. This may be achieved in general by gravity or in the convenient case of nucleic acids bound to magnetic glass particles by separating the nucleic acid bound to the magnetic glass particles by applying a magnetic field. For instance, the magnetic particles can be pulled to the wall of the vessel in which incubation was performed. The liquid containing the biological compounds or reaction components that were not bound to the magnetic particles can then be removed. The removal procedure used depends on the type of vessel in which incubation was performed. Suitable steps include removing the liquid via pipeting or aspiration. The material with the bound nucleic acid may then be washed at least once, preferably with a mixture of 70 volume parts ethanol with 30 volume parts water ("70% Ethanol") or in an acidic wash solution as described in WO 99/40098. A wash solution is used that does not cause the nucleic acids and the target nucleic acid to be released from the material surface but that washes away the undesired contaminants as thoroughly as possible. This wash step preferably takes place by incubating the glass or silica with the bound nucleic acid. The material is preferably re-suspended during this step. The contaminated wash solution is preferably removed just as in the binding step described above. After the last wash step, the material can be dried briefly in a vacuum, or the fluid can be allowed to evaporate. A pretreatment step using acetone may also be performed.

In an embodiment of the invention the nucleic is obtained from a biological sample using the solid phases according to the invention and methods known to the expert in the field. The biological sample comprises cells from multicellular organisms as e.g. human and animal cells such as Leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body. Preferably the biological sample is blood, blood plasma, blood serum or urine. The blood plasma is preferably EDTA-, heparin- or citrate-treated blood plasma. The biological sample comprising the nucleic acids is lysed to create a mixture of biological compounds comprising nucleic acids and other components. Procedures for lysing biological samples are known by the expert and can be chemical, enzymatic or physical in nature. A combination of these procedures is applicable as well. For instance, lysis can be performed using ultrasound, high pressure, shear forces, alkali, detergents or chaotropic saline solutions, or proteases or lipases. For the lysis procedure to obtain nucleic acids, special reference is made to Sambrook et al.: Molecular Cloning, A Laboratory Manual, 2nd Addition, Cold Spring Harbour Laboratory Press, Cold Spring Harbour, N.Y. and Ausubel et al.: Current Protocols in Molecular Biology 1987, 1. Wiley and Sons, NY. Then the nucleic acids are isolated from the lysis mixture using the methods and solid phases according to the invention and can then be subjected to the methods according to the invention, i.e. the bisulfite treatment according to the invention. Chaotropic agents are also used to lyse cells to prepare a mixture between nucleic acids and other biological substances (see e.g. Sambrook et al. (1989) or EP 0 389 063). Afterwards the material comprising glass or silica is added and a purification effect results from the behavior of DNA or RNA to bind to material with a glass surface under these conditions i.e. in the presence of certain concentrations of a chaotropic agent, higher concentrations of organic solvents or under acidic conditions. Therefore, the present invention also considers the combination of lysis steps and the bisulfite reaction, i.e. the nucleic acid isolated from the mixture between nucleic acids and other biological substances is directly subjected to the bisulfite treatment whereby the nucleic acid is bound to a solid phase during the deamination and/or the desulfonation step. In more detail, a method is provided for the conversion of cytosine bases in a nucleic acid to uracil bases whereby 5-methyl-cytosine bases are not significantly converted ("bisulfite reaction" or "bisulfite treatment") whereby the nucleic acid is isolated from a mixture comprising a nucleic acid and other biological compounds by binding it to a solid phase, preferably a material comprising glass or silica, and remains bound to the solid phase during the deamination and/or the desulfonation step of the bisulfite reaction. In even more detail, a method is provided wherein the nucleic acid is isolated from a mixture of a nucleic acid and other biological compounds and bound to a solid phase during the deamination and the desulfonation step of the bisulfite reaction, i.e. a method is provided for the conversion of cytosine bases in a nucleic acid to uracil bases whereby 5-methyl-cytosine bases are not significantly converted ("bisulfite reaction" or "bisulfite treatment") comprising the steps of a) providing a mixture of a nucleic acid and other biological compounds b) binding the nucleic acid to a solid phase, optionally removing the other biological compounds and optionally washing the solid phase bound nucleic acid, c) incubating the solid phase bound nucleic acid in the presence of sulfite ions whereby the nucleic acid is deaminated, d) optionally washing the deaminated solid phase bound nucleic acid, e) incubating the deaminated solid phase bound nucleic acid under alkaline conditions whereby the deaminated nucleic acid is desulfonated, f) optionally washing the deaminated and desulfonated solid phase bound nucleic acid, and g) optionally eluting the deaminated and desulfonated nucleic acid from the solid phase.

In another embodiment, a method is provided wherein the nucleic acid is isolated from a mixture of a nucleic acid and other biological compounds and is bound to a solid phase during the desulfonation step of the bisulfite reaction, i.e. a method is provided for the conversion of cytosine bases in a nucleic acid to uracil bases whereby 5-methyl-cytosine bases are not significantly converted ("bisulfite reaction" or "bisulfite treatment") comprising the steps of a) providing a mixture of a nucleic acid and other biological compounds b) binding the nucleic acid to a sold phase, optionally removing the other biological compounds, optionally washing the solid phase bound nucleic acid and eluting the nucleic acid from the solid phase, c) incubating the eluted nucleic acid in the presence of sulfite ions whereby the nucleic acid is deaminated, d) binding the deaminated nucleic acid to a solid phase, e) optionally washing the deaminated solid phase bound nucleic acid, f) incubating the deaminated solid phase bound nucleic acid under alkaline conditions whereby the deaminated nucleic acid is desulfonated, g) optionally washing the deaminated and desulfonated solid phase bound nucleic acid, and h) optionally eluting the deaminated and desulfonated nucleic acid from the solid phase.

In another embodiment of the invention, a method is provided wherein the nucleic acid is isolated from a mixture of a nucleic acid and other biological compounds and bound to a solid phase during the deamination step of the bisulfite reaction, i.e. a method is provided for the conversion of cytosine bases in a nucleic acid to uracil bases whereby 5-methyl-cytosine bases are not significantly converted, comprising the steps of a) providing a mixture of a nucleic acid and other biological compounds b) binding the nucleic acid to a solid phase, optionally removing the other biological compounds and optionally washing the solid phase bound nucleic acid, c) incubating the solid phase bound nucleic acid in the presence of sulfite ions whereby the nucleic acid is deaminated, d) optionally washing the solid phase bound nucleic acid,
e) eluting the deaminated nucleic acid from the solid phase,
f) incubating the deaminated nucleic acid under alkaline conditions whereby the deaminated nucleic acid is desulfonated.

The preferred method according to the invention further comprises the step of eluting the bound nucleic acid from said solid phase. Then said nucleic acid may be e.g. amplified. For elution to take place, the material comprising glass or silica (with the unmodified silica surface) is re-suspended in a solution with no or only a low amount of chaotropic agent and/or organic solvent. Alternatively, the suspension can be diluted with a solution with no or only a low amount of chaotropic agent and/or organic solvent. Buffers of this nature are known from DE 3724442 and Jakobi et al., supra. The elution buffers with a low salt content are in particular buffers with a content of less than 0.2 mol/l. In an especially preferred embodiment, the elution buffer contains the substance Tris for buffering purposes, in particular a Tris buffered solution with a pH around 7 or above 7. In another special embodiment, the elution buffer is demineralized water. The solution containing the nucleic acid is now ready to be used in the amplification reaction after the solid phase has been removed. Therefore, the nucleic acid is transferred to a new reaction tube containing all reagents necessary for amplification. Optionally, a solution containing all reagents necessary for amplification is added to the suspension of the solid phase and the released nucleic acids. In another embodiment, a solution containing all reagents necessary for amplification is added to the suspension of the solid phase and the bound nucleic acid without elution step whereby an amplification of the nucleic acid on the solid phase is performed.

According to the present invention, for washing and binding steps, preferably liquids are used which are suitable for processes in molecular biology, in particular desoxyribonucleic acid (DNA) or ribonucleic acid (RNA) purification processes which make use of the binding of these substances to a solid phase, in particular silica or glass surfaces, more particularly magnetic glass particles under certain conditions. Preferred liquids comprise alcohols and/or ketones or any mixtures thereof with water. Alcohols shall include according to the invention preferably primary, secondary or tertiary alcohols of the general formula R—OH where the R stands for the general formula -(—$CH_2$)$_n$—$CH_3$ with n>=0. However, other alcohols can also be used if they are suitable for molecular biology purposes as e.g. glycerol. Particularly suitable are the alcohols isopropanol, ethanol or mixtures thereof with water, preferably a mixture of 80 volume parts of isopropanol with 20 volume parts of water. In another embodiment of the invention the liquid comprises ketones as e.g. acetone. Further, suitable aqueous buffered solutions are used. Buffer systems which are suitable for molecular biology purposes may be found e.g. in Sambrook, J., et al., in "Molecular Cloning: A Laboratory Manual" (1989), Eds. J. Sambrook, E. F. Fritsch and T. Maniatis, Cold Spring Harbour Laboratory Press, Cold Spring Harbour, N.Y. Preferred buffer substances are Tris-hydroxymethylamine (TRIS), phosphate, N-(2-hydroxy-ethyl) piperazine-N'-(2-ethanesulfonic acid) (HEPES), salts thereof or other suitable substances. Additionally, substances may be present which modify the ionic strength of the solution as e.g. NaCl, KCl or $CaCl_2$ or which are metal cation complexing agents as e.g. ethylene-diamine-tetra acetic acid (EDTA) or the salts thereof.

In a preferred embodiment of the invention, the nucleic acid is amplified with the polymerase chain reaction (PCR; EP 201 184, EP-A-0 200 362, U.S. Pat. No. 4,683,202). The amplification method may also be the ligase Chain Reaction (LCR, Wu, D. Y. and Wallace, R. B., Genomics 4 (1989) 560-9 and Barany, F., Proc Natl Acad Sci USA 88 (1991) 189-93; Polymerase Ligase Chain Reaction (Barany, F., PCR Methods Appl 1 (1991) 5-16); Gap-LCR (PCT Patent Publication No. WO 90/01069); Repair Chain Reaction (European Patent Publication No. EP 439,182 A2), 3SR (Kwoh, D. Y., et al., Proc Natl Acad Sci USA 86 (1989) 1173-7; Guatelli, J. C., et al., Proc Natl Acad Sci USA 87 (1990) 1874-8; PCT Patent Publication No. WO 92/0880A), and NASBA (U.S. Pat. No. 5,130,238). Further, there are strand displacement amplification (SDA), transcription mediated amplification (TMA), and Qβ-amplification (for a review see e.g. Whelen, A. C. and Persing, D. H., Annu Rev Microbiol 50 (1996) 349-73; Abramson, R. D. and Myers, T. W., Curr Opin Biotechnol 4 (1993) 41-7). Particularly preferred amplification methods according to the invention are the methylation specific PCR method (MSP) disclosed in U.S. Pat. No. 5,786,146 which combines bisulfite treatment and allele-specific PCR (see e.g. U.S. Pat. No. 5,137,806, U.S. Pat. No. 5,595,890, U.S. Pat. No. 5,639,611).

In a preferred embodiment, the method may further comprise the step of detecting the amplified nucleic acid. The amplified nucleic acid may be determined or detected by standard analytical methods known to the person skilled in the art and described e.g. in Sambrook, et al., Molecular Cloning, Cold Spring Harbor University Press (1989), Lottspeich and Zorbas, in "Bioanalytik" (1998), Eds. L. a. Zorbas, Spektrum Akademischer Verlag, Heidelberg, Berlin, Germany, or in Ausubel, F., et al., in "Current protocols in molecular biology" (1994), Eds. F. Ausubel, R. Brent and K. R. E., Wiley & Sons Verlag, New York. There may be also further purification steps before the target nucleic acid is detected e.g. a precipitation step. The detection methods may include but are not limited to the binding or intercalating of specific dyes as ethidium bromide which intercalates into the double-stranded DNA and changes its fluorescence thereafter. The purified nucleic acids may also be separated by electrophoretic methods optionally after a restriction digest and visualized thereafter. There are also probe-based assays which exploit the oligonucleotide hybridisation to specific sequences and subsequent detection of the hybrid. It is also possible to sequence the target nucleic acid after further steps known to the expert in the field. Other methods apply a diversity of nucleic acid sequences to a silicon chip to which specific probes are bound and yield a signal when a complementary sequences bind.

In a particularly preferred embodiment of the invention, the nucleic acid is detected by measuring the intensity of fluorescence light during amplification. This method entails the monitoring of real time fluorescence. A particularly preferred method exploiting simultaneous amplification and detection by measuring the intensity of fluorescent light is the TaqMan® method disclosed in WO 92/02638 and the corresponding U.S. Pat. No. 5,210,015, U.S. Pat. No. 5,804,375, U.S. Pat. No. 5,487,972. This method exploits the exonuclease activity of a polymerase to generate a signal. In detail, the nucleic acid is detected by a process comprising contacting the sample with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TaqMan® technology eliminates the need for a solid phase bound reaction complex to be formed and made detectable. In more general terms, the amplification and/or detection reaction of the method according to the invention is a homogeneous solution-phase assay. Further preferred method are the formats used in the LightCyder® instrument (see e.g. U.S. Pat. No. 6,174,670). Particularly preferred is the use of bisulfite treatment, amplification with or without methylation specific primers in the presence of a methylation-specific probe and real-time fluorescence detection as described in U.S. Pat. No. 6,331,393.

In a preferred embodiment of the present invention, the method is automated, i.e. the method carries out an automatable process as e.g. described in WO 99/16781. Automatable process means that the steps of the process are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. In a preferred embodiment of the invention, the method is in a high-throughput format, i.e. the automated methods is carried out in a high-throughput format which means that the methods and the used machine or apparatus are optimized for a high-throughput of samples in a short time.

Preferably the method according to the invention is used in diagnostics, for diagnostic analysis or for bioanalytics, or for the screening of tissue or fluids from the human or even animal body for the presence of certain methylation pattern. Further, the method according to the invention is used to enhance the speed, accuracy or sensitivity of the detection of methylation sites in nucleic acids.

In a preferred embodiment, the present invention is directed to the use of a solid phase in the deamination and/or desulfonation step of a reaction wherein cytosine bases in a nucleic acid are converted to uracil bases in the presence of bisulfite ions whereby 5-methyl-cytosine bases are not significantly converted ("bisulfite reaction"). In a preferred embodiment, the present invention is directed to the use of a solid phase in the deamination and/or desulfonation step of reaction wherein cytosine bases in a nucleic acid are converted to uracil bases in the presence of bisulfite ions whereby 5-methyl-cytosine bases are not significantly converted. More particularly, this means that the solid phase is used to bind the nucleic acid during the deamination and/or the desulfonation step of the bisulfite reaction, i.e. the nucleic acid is bound to the solid phase during the deamination and/or desulfonation step of the bisulfite reaction. Preferably, the solid phase is a material comprising silica or glass. More preferably, solid phase is a glass fleece or a glass membrane. In the most preferred embodiment the solid phase is a magnetic glass particle.

In another preferred embodiment, the present invention is directed to a kit for performing a bisulfite reaction containing a solution comprising bisulfite ions and a solid phase. In a preferred embodiment the solid phase is a material comprising silica or glass. In a more preferred embodiment, the solid phase is a glass fleece or a glass membrane. In the most preferred embodiment, the solid phase is a magnetic glass particle. In another embodiment of the invention a kit of parts is provided which comprises a storage container containing the magnetic glass particles or a suspension thereof according to the present invention. Such kits known in the art further comprise plastics ware which may be used during the bisulfite procedure as e.g. microtiter-plates in the 96 or 384 well format or reaction tubes manufactured e.g. by Eppendorf, Hamburg, Germany. The kit may further comprise a washing solution which is suitable for the washing step of the solid phase, in particular, the glass fleece or membrane or the magnetic glass particles. Often the washing solution is provided as a stock solution which has to be diluted before the use. The kit may further comprise an eluant, i.e. a solution or a buffer (e.g. TE, 10 mM Tris, 1 mM EDTA, pH 8.0) or pure water to elute the DNA or RNA bound to the solid phase. Further, additional reagents may be present which contain buffers suitable for use in the present invention. Preferably, the kit according to the invention is used for a reaction wherein cytosine bases in a nucleic acid are converted to uracil bases in the presence of bisulfite ions whereby 5-methyl-cytosine bases are not significantly converted.

The following examples, references and figures are provided to aid the understanding of the present invention, the true scope of which is set forth in the appended claims. It is understood that modifications can be made in the procedures set forth without departing from the spirit of the invention.

EXAMPLES

1. Example 1

Establishment of a LC-PCR Specific for Bisulphite Treated DNA 1.1 General

The fact that the bisulfite reaction has worked and converted non-methylated cytosines to uracil can be demonstrated by a polymerase chain reaction whereby primers are used which are specific to a region of the nucleic acid sequence wherein non-methylated cytosines have been converted to uracils, i.e. the base adenine in the primer is opposite to the uracil being the bisulfite reaction product from non-methylated cytosines. In case of incomplete conversion, the primer could not hybridize to this region as there would be cytosines not matching the adenine bases in the primer. This would have the effect that no PCR product would be obtained.

An improved method to perform rapid polymerase chain reactions is disclosed e.g. in U.S. Pat. No. 6,174,670 and is used in the LightCycler® instrument (Roche, Mannheim, Germany). In this method, two labeled probes can come into close proximity in an amplificate dependent manner so that the two labels can perform a fluorescence energy transfer (FRET). The amount of the amplificate thereby correlates with the intensity of the emitted light of a certain wavelength. This specific PCR method can therefore be used to analyze whether a complete conversion of non-methylated cytosines was obtained, by e.g. analyzing the promoter region of the glutathion-S-transferase π gene (see e.g. SEQ ID NO: 1 for the full length sequence of this gene and the promoter, U.S. Pat. No. 5,552,277, Genbank accession code M24485 and Morrow et al. (1989) Gene 75, 3-11) using suitable probes and primers. However, the expert skilled in the art knows that other methods can be used for this evaluation as well. Fluorescence measurements are normalized by dividing by an initial fluorescence measurement, i.e., the background fluorescence, obtained during a cycle early in the reaction while the fluorescence measurements between cycles appear to be relatively constant. The cycle number chosen for the initial fluorescence measurement is the same for all reactions compared, so that all measurements represent increases relative to the same reaction cycle. In the early cycles of a polymerase chain reaction amplification, the number of target molecules can be described by the geometric equation $N_i = N_o \times (1+E)^i$, where $N_o$=the number of target molecules at the start of the reaction, $N_i$=the number of target molecules at the completion of the i-th cycle, E=the efficiency of the amplification (0=<E=<1). During this geometric growth phase of the amplification, the number of cycles required to reach a particular threshold value ($C_T$ value or crossing point) is inversely proportional to the logarithm of (1+E). Thus, the $C_T$ value represents a measure of the reaction efficiency that allows comparisons between reactions. A decrease in the $C_T$ value, which means that the reaction reached the threshold value in fewer cycles, indicates an increase in reaction efficiency. As the increase in amplification product is monitored by measuring the increase in reaction fluorescence, the $C_T$ is defined herein as the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau. An AFL of 1.5 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ value or crossing point, was calculated by interpolating fluorescence measurements between cycles.

1.2 General Methodology

The following experiment demonstrates that the described PCR on the LightCycler® instrument can be used as an evaluation tool for bisulfite treated DNA. It shows that the designed primer/probe combination gives positive results only with DNA after bisulfite treatment. Bisulfite treated DNA (in this case bisulfite DNA was treated according to the protocol described in example 2) and untreated DNA were amplified in parallel using the same template concentrations (20 ng and 1 ng per PCR).

1.3 PCR analysis on the LightCycler® instrument 1.3.1 Composition of Mastermix:

LC FastStart DNA Master HybridizationProbe 1×, 2 mM MgCl2, forward Primer 0.5 µM, reversed Primer 0.5 µM, donor probe 250 nM, acceptor probe 250 nM, template 10 µl, total PCR volume 20 µl.

1.3.2 PCR-Conditions:

| Denaturation 10 min/95° C. | |
| --- | --- |
| 55 cycles | 95° C./10 s |
| | 65° C./10 s - signal acquisition |
| | 72° C./10 s Ramp time 20° C./s |

1.4 Result

| MDNA/PCR | Bisulphite treatment | $C_T$-Value or Crossingpoint |
| --- | --- | --- |
| 20 ng | Yes | 30.55 |
| | | 29.72 |
| | | 29.95 |
| | | 30.06 |
| 1 ng | yes | 34.7 |
| | | 35.8 |
| | | 34.07 |
| | | 33.86 |
| 20 ng | No | No growth curve |
| | | No growth curve |
| | | No growth curve |
| | | No growth curve |
| 1 ng | No | No growth curve |
| | | No growth curve |
| | | No growth curve |
| | | No growth curve |

The result shows crossing points only for bisulfite treated DNA. Therefore this PCR is suitable in evaluating bisulfite methods. For those skilled in the art it is clear that any PCR might be used as an evaluation tool if it is guaranteed that the primer/probe combination does not react with DNA before bisulfite treatment.

2. Example 2

Bisulfite Reaction Using Magnetic Glass Particles (MGPs)

2.1.1 Denaturation of DNA:

100 µl of methylated DNA (Intergen, distributed by Serologicals Corporation, Norcross, Ga., USA; Cat S 7821) dilution (30 ng and 6 ng/assay spiked in 1000 ng hDNA background Roche Cat. 1691112; 10 replicates per concentration), and 12 µl 2 M NaOH are mixed and incubated for 15 min at 37° C.

2.1.2 Deamination of DNA

112 µl of the denatured DNA are mixed with 200 µl bisulfite reagent (2.5M sodium disulfite, 125 mM hydroquinone, pH 5.0) and incubated for 16 h at 50° C.

2.2 Processing using MGPs

312 µl of the deaminated DNA are mixed with 600 µl binding buffer (MagNAPure DNA Isolation Kit I, Roche Cat. Nr. 3 003 990) and 75 µl magnetic glass particle solution (MagNAPure DNA Isolation Kit I) and incubated for 15 min/room temperature with continuous mixing. Thereafter, the magnetic glass particles are washed three times with 1 ml 70% Ethanol. Bound free separation is done in a magnetic separator (Roche Cat. 1641794). Thereafter, desulphonation takes place by adding 250 µl 90% EtOH/20 mM NaOH to the DNA bound to the MGPs; the mixture is incubated for 10 min at room temperature with mixing. Thereafter the MGPs are washed two times with 90% Ethanol. To get rid of ethanol rests the MGPs were heated for 15 min./60° C. in a thermomixer with open lid. Thereafter the DNA is eluted with 50 µl 10 mM Tris/0.1 mM EDTA pH 7.5 (15 min./60° C.). 10 µl of the eluted DNA is used for subsequent PCR analysis.

2.3 Bisulphite Treatment Using the Intergen Kit 30 ng and 6 ng of methylated DNA (Intergen, distributed by Serologicals Corporation, Norcross, Ga., USA; Cat. S7821) were treated (10 replicates per concentration) according to the method described in the package insert of the Intergen CpGenome DNA Modification Kit (Intergen, distributed by Serologicals Corporation, Norcross, Ga., USA; Cat. S7820). 10 µl of the eluted DNA is used for subsequent PCR analysis.

2.4 Detection of the Bisulphite Treated DNA by Using a Specific PCR on the LightCycler® Instrument (Hyprobe-Format)

2.4.1 Composition of Mastermix

LightCycler® FastStart DNA Master HybridizationProbe 1× (Roche 2239272), 2 mM MgCl2, forward Primer 0.5 µM, reversed Primer 0.5 µM, donor probe 250 nM, acceptor probe 250 nM, template 10 µl, total PCR volume 20 µl.

2.4.2 PCR-Conditions

Denaturation 10 min/95° C.
55 cycles 95° C./10 s
65° C./10 s—signal acquisition
72° C./10 s Ramp time 20° C./s Samples from MGP bisulfite treatment and Intergen bisulfite treatment were run in parallel in the same run on the LightCycler® instrument.

2.4.3 Results:

|  | Methylated DNA per | | Bisulfite Method used | |
|---|---|---|---|---|
|  |  |  | Intergen | MGP method |
| replicates | Bisulfite | PCR | $C_T$-Values or Crossing points | |
| 1 | 30 ng | 6 ng | 29.90 | 30.46 |
| 2 |  |  | 30.07 | 29.86 |
| 3 |  |  | 30.07 | 30.44 |
| 4 |  |  | 30.14 | 30.35 |
| 5 |  |  | 30.22 | 30.24 |
| 6 |  |  | 30.26 | 30.46 |
| 7 |  |  | 30.31 | 30.50 |
| 8 |  |  | 30.19 | 30.54 |
| 9 |  |  | 30.03 | 30.17 |
| 10 |  |  | 29.85 | 30.69 |
| 1 | 6 ng | 1.2 ng | 32.49 | 32.14 |
| 2 |  |  | 32.67 | 32.60 |
| 3 |  |  | 32.29 | 32.83 |
| 4 |  |  | 32.87 | 32.53 |
| 5 |  |  | 32.15 | 32.90 |
| 6 |  |  | 32.23 | 32.77 |
| 7 |  |  | 32.59 | 32.73 |
| 8 |  |  | 32.91 | 33.09 |
| 9 |  |  | 32.46 | 32.88 |
| 10 |  |  | 33.17 | 32.83 |

The $C_T$-values or crossing points calculated during real time PCR are almost identical for both bisulfite methods used, i.e. that the performance of the methods is the same.

3 Example 3

Automated Bisulphite Reaction Using MGPs 3.1 Performance of Bisulphite Reaction 3.1.1 Denaturation of DNA:

20 µl of methylated DNA (Intergen, distributed by Serologicals Corporation, Norcross, Ga., USA; Cat. S7821) dilution (50 ng/assay), 4 µl of a Poly (dA) solution (concentration 250 ng/µl) and 2.6 µl 2 M NaOH are mixed and incubated for 10 min at 37° C.

3.1.2 Deamination of DNA

26 µl of the denatured DNA are mixed with 220 VI bisulfite reagent (2.5M Sodium bisulfite, 125 mM hydroquinone, pH 5.0) and incubated for 4 h at 50° C.

3.1.3 Automated Processing Using the MagnaPure LC-Instrument

250 µl of the deaminated DNA are mixed with 600 µl binding buffer (MagNAPure DNA Isolation Kit I, Roche, Mannheim, Germany) and 75 µl magnetic glass particle solution (MagNAPure DNA Isolation Kit I, Roche, Mannheim, Germany) and incubated for 15 min/room temperature with continuous mixing. Thereafter, the magnetic glass particles are washed three times with 1 ml 70% Ethanol. Thereafter, desulphonation takes place by adding 250 µl 90% EtOH/20 mM NaOH to the DNA bound to the MGPs; the mixture is incubated for 10 min at room temperature with mixing. Thereafter the MGPs are washed two times with 90% Ethanol and are eluted with 50 µl 10 mM Tris/0.1 mM EDTA pH 7.5 (7 min./80° C.).

3.1.4 Detection of the Bisulphite Treated DNA by Using a Specific PCR on the LightCycler® Instrument (Hyprobe-Format)

3.1.4.1 Composition of Mastermix:

LightCycler® FastStart DNA Master HybridizationProbe 1×, 2 mM MgCl2, forward Primer 0.5 µM, reversed Primer 0.5 µM, donor probe 250 nM, acceptor probe 250 nM, template 5 µl, total PCR volume 201 µl.

3.1.4.2 PCR-Conditions:

| Denaturation 10 min/95° C. | |
|---|---|
| 55 cycles | 95° C./10 s |
|  | 65° C./10 s - signal acquisition |
|  | 72° C./10 s Ramp time 20° C./s |

3.1.4.3 Results

| Template | ng DNA Per bisulphite assay | ng DNA per PCR | Crossingpoint |
|---|---|---|---|
| Univers. Methylated DNA | 100 | 10 | 33.97 |
|  |  |  | 36.66 |
| Univers. Methylated DNA | 50 | 5 | 35.66 |
|  |  |  | 35.82 |
|  |  |  | 37.67 |
|  |  |  | 38.37 |
| Univers. Methylated DNA | 10 | 1 | 37.82 |
|  |  |  | 39.89 |
|  |  |  | 38.76 |
|  |  |  | 39.85 |

The result shows crossing points for each concentration used. This means that the automated bisulfite treatment was successful

4. Example 4

Performance of Bisulfite Reactions Using Glass Fleece 4.1 Denaturation of DNA 100 µl methylated DNA (Intergen, distributed by Serologicals Corporation, Norcross, Ga., USA; Cat. S7821) dilution (30 and 6 ng/assay, 10 replicates per concentration) are mixed with 12 µl 2 M NaOH and incubated for 15 min at 37° C.

4.2 Deamination of DNA:

112 µl of denatured DNA are incubated with 200 µl bisulfite reagent (2.5 M sodium bisulfite, 125 mM hydroquinone, pH 5.0) for 16 h/50° C. with continuous mixing.

4.3 Processing of Deaminated DNA with the High Pure PCR Template Preparation Kit (Roche Cat. 1 796 828)

- 312 µl deaminated DNA are mixed with 2001 binding buffer from the kit and 100 µl Isopropanol and pipetted on to the column with the glass fleece. The column is then centrifuged in an Eppendorf table top centrifuge (1 min/8000 rpm).
- Thereafter the columns are washed three times each with 500 µl 80% Ethanol (centrifugation 10 sec/12000 rpm)
- For desulfonation 250 µl reagent (38% Ethanol/100 mM NaCl/200 mM NaOH) is added to the columns. After an incubation of 5 min/room temperature centrifuge 1 min/800 rpm.
- Thereafter the columns are washed two times each with 500 µl 80% ethanol (centrifugation 10 sec/12000 rpm)
- Finally the bound DNA is eluted by adding 50 µl pre-warmed (70° C.) elution buffer (10 mM Tris/0.1 mM EDTA pH 7.5) and centrifugation for 1 min/800 rpm.

4.4 Detection of the Bisulfite Treated DNA by Using a Specific PCR on the LightCycler® Instrument (Hyprobe-Format)

4.4.1 Composition of Mastermix:

LightCycler® FastStart DNA Master HybridizationProbe 1× (Roche 2239272), 2 mM MgCl$_2$, forward Primer 0.5 µM, reversed Primer 0.5 µM, donor probe 250 nM, acceptor probe 250 nM, template 10 µl, total PCR volume 20 µl.

4.4.2 PCR-Conditions:

| Denaturation 10 min/95° C. | |
| --- | --- |
| 55 cycles | 95° C./10 s |
| | 65° C./10 s - signal acquisition |
| | 72° C./10 s Ramp time 20° C./s |

4.4.3 Results:

| Methylated DNA per | | |
| --- | --- | --- |
| Bisulfite Assay | PCR | $C_T$-values or crossingpoints |
| 30 ng | 6 ng | 32.27 |
| | | 32.01 |
| | | 31.89 |
| | | 33.23 |
| | | 32.18 |
| | | 32.63 |
| | | 32.65 |
| | | 32.26 |
| | | 32.00 |
| | | 31.84 |
| 6 ng | 1.2 ng | 34.28 |
| | | 35.70 |
| | | 35.52 |
| | | 36.23 |
| | | 35.05 |
| | | 35.60 |
| | | 34.75 |
| | | 34.86 |
| | | 34.80 |
| | | 34.93 |

The result shows crossing points for each concentration used. This means that the bisulfite treatment using glass fleeces was successful.

5. Example 5

Performance of Bisulfite Reaction on Glass Fleece Solid Phase 5.1 Binding of DNA to Glass Fleece 100 µl DNA (containing a mixture of 1 µg hDNA (Roche) and 100 ng methylated DNA (Intergen, distributed by Serologicals Corporation, Norcross, Ga., USA; Cat. S7821) are mixed with 200 µl binding buffer (High Pure PCR Template Preparation Kit, Roche Cat. 1796828) and 100 µl isopropanol. The mixture is pipetted on to the column from the kit. The column is then centrifuged in an Eppendorf table top centrifuge (1 min/8000 rpm). The fleece is washed two times with washing buffer from the kit (500 µl per wash step).

5.2 Denaturation of DNA Bound to Glass Fleece

Denaturation takes place by pipetting 200 µl of 38% EtOH/100 mM NaOH/200 mM NaCl to the glass fleece and incubating both for 10 min. at room temperature. Thereafter the fleece is washed once with 500 µl of washing buffer from the kit.

5.3 Desamination of DNA Bound to Glass Fleece:

200 µl of desaminating solution (6.25M urea/2M sodium bisulfite/pH 5.0) are pipetted to the fleece with the DNA followed by an incubation at 50° C. for 16 h in a water bath. Thereafter the desaminating reagent is removed and the fleece is washed twice with each 500 µl washing buffer from the kit.

5.4 Desulfonation of Deaminated DNA Bound to Glass Fleece

For desulfonation 250 µl reagent (90% Ethanol/20 mM NaOH) is added to the columns. After an incubation of 15 min/room temperature the columns are centrifuged 1 min/800 rpm. Thereafter the columns are washed two times each with 500 µl 80% ethanol (centrifugation 10 sec/12000 rpm)

5.5 Elution DNA

Finally the bound DNA is eluted by adding 50 µl pre-warmed (70° C.) elution buffer (10 mM Tris/0.1 mM EDTA pH 7.5) and centrifugation for 1 min/8000 rpm.

5.6 Detection of the Bisulfite Treated DNA by Using a Specific PCR on the LightCycler Instrument (Hyprobe-Format)

5.6.1 Composition of Mastermix:

LightCycler FastStart DNA Master HybridizationProbe 1× (Roche 2239272), 2 mM MgCl2, forward Primer 0.5 µM, reversed Primer 0.5 µM, donor probe 250 nM, acceptor probe 250 nM, template 10 µl, total PCR volume 20 µl.

5.6.2 PCR-Conditions:

| Denaturation 10 min/95° C. | |
| --- | --- |
| 55 cycles | 95° C./10 s |
| | 65° C./10 s - signal acquisition |
| | 72° C./10 s Ramp time 20° C./s |

5.6.3 Result:

| Sample number | Methylated DNA per PCR | Crossing Point |
| --- | --- | --- |
| 1 | 20 ng | 34.90 |
| 2 | 20 ng | 35.27 |
| 3 | 20 ng | 36.09 |
| 4 | 20 ng | 36.80 |

In each reaction a growth curve was detected and the crossing point was calculated. This result shows that desamination and desulfonation on the glass fleece solid phase is feasible.

LIST OF REFERENCES

Abramson, R. D. and Myers, T. W., Curr Opin Biotechnol 4 (1993) 41-7
Alderton, R. P., et al., Anal Biochem 201 (1992) 166-9
Ausubel, F., et al., in "Current protocols in molecular biology" (1994), Eds. F. Ausubel, R. Brent and K. R. E., Wiley & Sons Verlag, New York
Barany, F., PCR Methods Appl 1 (1991) 5-16
Barany, F., Proc Natl Acad Sci USA 88 (1991) 189-93
Benyajati, C., et al., Nucleic Acids Res 8 (1980) 5649-67
Braunauer, in "The Adsorption of Gases and Vapors" (1943), Princeton University Press
Clark, S. J., et al., Nucleic Acids Res 22 (1994) 2990-7
DE 3724442
DE-A 37 34 442
EP 0 200 362
EP 0 201 184
EP 0 389 063
EP 0 439 182
Feil, R., et al., Nucleic Acids Res 22 (1994) 695-6
Frommer, M., et al., Proc Natl Acad Sci USA 89 (1992) 1827-31
GB 91/00212
Grigg, G. and Clark, S., Bioessays 16 (1994) 431-6
Grigg, G. W., DNA Seq 6 (1996) 189-98
Grunau, C., et al., Nucleic Acids Res 29 (2001) E65-5
Guatelli, J. C., et al., Proc Natl Acad Sci USA 87 (1990) 1874-8
Jakobi, R., et al., Anal Biochem 175 (1988) 196-201
Komiyama, M. and Oshima, S., Tetrahedron Letters 35 (1994) 8185-8188
Kwoh, D. Y., et al., Proc Natl Acad Sci USA 86 (1989) 1173-7
Lottspeich and Zorbas, in "Bioanalytik" (1998), Eds. L. a. Zorbas, Spektrum Akademischer Verlag, Heidelberg, Berlin, Germany
Marko, M. A., et al., Anal Biochem 121 (1982) 382-7
Morrow, C. S., et al., Gene 75 (1989), 3-11
Oakeley, E. J., Pharmacol Ther 84 (1999) 389-400
Olek, A., et al., Nucleic Acids Res 24 (1996) 5064-6
Paulin, R., et al., Nucleic Acids Res 26 (1998) 5009-10
Raizis, A. M., et al., Anal Biochem 226 (1995) 161-6
Sambrook, J., et al., in "Molecular Cloning: A Laboratory Manual" (1989), Eds. J. Sambrook, E. F. Fritsch and T. Maniatis, Cold Spring Harbour Laboratory Press, Cold Spring Harbour, N.Y.
Spray Drying Handbook (1991), John Wiley & Sons, New York
U.S. Pat. No. 4,683,202
U.S. Pat. No. 5,130,238
U.S. Pat. No. 5,137,806
U.S. Pat. No. 5,210,015
U.S. Pat. No. 5,234,809
U.S. Pat. No. 5,487,972
U.S. Pat. No. 5,552,277
U.S. Pat. No. 5,595,890
U.S. Pat. No. 5,639,611
U.S. Pat. No. 5,786,146
U.S. Pat. No. 5,804,375
U.S. Pat. No. 6,174,670
U.S. Pat. No. 6,331,393
Vogelstein, B. and Gillespie, D., Proc Natl Acad Sci USA 76 (1979) 615-9
Warnecke, P. M., et al., Methods 27 (2002) 101-7
Whelen, A. C. and Persing, D. H., Annu Rev Microbiol 50 (1996) 349-73
WO 00/32762
WO 00/37291
WO 01/37291
WO 01/98528
WO 02/31186
WO 90/01069
WO 90/06045
WO 92/02638
WO 92/0880A
WO 96/41811
WO 99/16781
WO 99/40098
Wu, D. Y. and Wallace, R. B., Genomics 4 (1989) 560-9

We claim:

1. A method for the conversion of cytosine bases in a DNA molecule to uracil bases, comprising:
   a) binding a double stranded DNA directly to an unmodified solid phase without a compound mediating the binding to the solid phase, wherein the unmodified solid phase is selected from the group consisting of glass, silica, and a glass or silica containing material,
   b) denaturing the double stranded DNA,
   c) incubating the solid phase bound DNA in the presence of sulfite ions whereby the DNA is deaminated, yielding a solid phase bound deaminated DNA,
   d) optionally washing the solid phase bound deaminated DNA,
   e) incubating the solid phase bound deaminated DNA under alkaline conditions whereby the deaminated DNA is desulfonated,
   f) washing the solid phase bound deaminated and desulfonated DNA, and
   g) eluting the washed deaminated and desulfonated DNA from the solid phase.

2. A method for conversion of cytosine bases in a DNA molecule to uracil bases comprising:
   a) binding a double stranded DNA directly to an unmodified solid phase without a compound mediating the binding to the solid phase, wherein the unmodified solid phase is selected from the group consisting of glass, silica, and glass or silica containing material,
   b) denaturing the double stranded DNA,
   c) incubating the solid phase bound DNA in the presence of sulfite ions whereby the DNA is deaminated, yielding a solid phase bound deaminated DNA,
   d) washing the solid phase bound deaminated DNA,
   e) eluting the washed deaminated DNA from the solid phase, and
   f) incubating the deaminated DNA under alkaline conditions whereby the deaminated DNA is desulfonated.

3. The method according to claim 1 or 2 wherein the solid phase is a glass fleece or a glass membrane.

4. The method according to claim 1 or 2 wherein the solid phase is a magnetic glass particle.

5. The method according to claim 4 wherein the magnetic glass particle has a mean diameter between 0.5 μm and 5 μm.

6. The method according to claim 4 wherein the magnetic glass particle contains a magnetic object with a diameter between 5 and 500 nm.

7. The method according to claim 4 wherein the magnetic glass particle contains a magnetic object with a mean diameter of 23 nm.

8. The method according to claim 4 wherein the magnetic glass particle is manufactured by the sol-gel method.

9. The method according to claim 8, wherein said sol-gel method comprises:
   a) suspending magnetic objects in a sol,
   b) hydrolyzing the sol to cover the magnetic objects with a gel,
   c) spray-drying the magnetic objects covered with a gel in a two-nozzle spray-drier, and
   d) sintering the spray-dried powder to form a glass from the gel covering the magnetic objects.

10. The method of claim 1, wherein the denaturing in method step b) is performed in the presence of NaOH.

11. A method for the conversion of cytosine bases in a DNA molecule to uracil bases, comprising:
   a) denaturing a double stranded DNA,
   b) incubating denatured double stranded DNA in the presence of sulfite ions whereby the DNA is deaminated, yielding a deaminated DNA,
   c) binding the deaminated double stranded DNA directly to an unmodified solid phase without a compound mediating the binding to the solid phase, wherein the unmodified solid phase is selected from the group consisting of glass, silica, and a glass or silica containing material,
   d) optionally, washing the solid phase bound deaminated DNA,
   e) incubating the solid phase bound deaminated DNA under alkaline conditions whereby the deaminated DNA is desulfonated,
   f) washing the solid phase bound deaminated and desulfonated DNA, and
   g) eluting the washed deaminated and desulfonated DNA from the solid phase.

* * * * *

SEQUENCE LISTING

```
<160> NUMBER OF SEQ ID NOS: 1

<210> SEQ ID NO 1
<211> LENGTH: 4261
<212> TYPE: DNA
<213> ORGANISM: Homo sapiens
<220> FEATURE:
<221> NAME/KEY: misc_signal
<222> LOCATION: (1156)..(1162)
<223> OTHER INFORMATION: transcription regulatory motif; putative
<220> FEATURE:
<221> NAME/KEY: GC_signal
<222> LOCATION: (1169)..(1174)
<220> FEATURE:
<221> NAME/KEY: GC_signal
<222> LOCATION: (1179)..(1184)
<220> FEATURE:
<221> NAME/KEY: TATA_signal
<222> LOCATION: (1194)..(1198)
<220> FEATURE:
<221> NAME/KEY: exon
<222> LOCATION: (1225)..(1254)
<220> FEATURE:
<221> NAME/KEY: polyA_signal
<222> LOCATION: (4041)..(4046)
<300> PUBLICATION INFORMATION:
<308> DATABASE ACCESSION NUMBER: Genbank:M24485
<309> DATABASE ENTRY DATE: 2000-03-04
<300> PUBLICATION INFORMATION:
<301> AUTHORS: Morrow et al.
```

```
<302> TITLE: Structure of the human genomic glutathione
      S-transferase-rr-gene
<303> JOURNAL: Gene
<304> VOLUME: 75
<305> ISSUE: 1
<306> PAGES: 3-11
<307> DATE: 1989-10-04
<300> PUBLICATION INFORMATION:
<310> PATENT DOCUMENT NUMBER: US5552277
<311> PATENT FILING DATE: 1994-07-19
<312> PUBLICATION DATE: 1996-09-03

<400> SEQUENCE: 1
aacaagagat caatatctag aataaatgga gatctgcaaa tcaacagaaa gtaggcagca        60
aagccaaaga aaatagccta aggcacagcc actaaaagga acgtgatcat gtcctttgca       120
gggacatggg tggagctgga agccgttagc ctcagcaaac tcacacagga acagaaaacc       180
agcgagaccg catggtctca cttataagtg ggagctgaac aatgagaaca catggtcaca       240
tggcggcgat caacacacac tggtgcctgt tgagcggggt gctggggagg gagagtacca       300
ggaagaatag ctaagggata ctgggcttaa tacctgggtg atgggatgat ctgtacagca       360
aaccatcatg gcgcacacac ctatgtaaca aacctgcaca tcctgcacat gtaccccaga       420
acttcaaata aaagttggac ggccaggcgt ggtggctcac gcctgtaatc ccagcacttt       480
gggaagccga ggcgtgcaga tcacctaagg tcaggagttc gagaccagcc cggccaacat       540
ggtgaaaccc cgtctctact aaaaatacaa aaatcagcca gatgtggcac gcacctataa       600
ttccacctac tcgggaggct gaagcagaat tgcttgaacc cgagaggcgg aggttgcagt       660
gagccgccga gatcgcgcca ctgcactcca gcctgggcca gcgtgaga ctacgtcata       720 aaataaaata aataacaca aataaaata aataaaata aataaaata aataataaa       780 ataaaataaa ataaaataaa ataaaataaa ataaagcaat ttcctttcct ctaagcggcc       840 tccaccctc tcccctgccc tgtgaagcgg gtgtgcaagc tccgggatcg cagcggtctt       900
agggaatttc ccccgcgat gtccggcgc gccagttcgc tgcgcacact tcgctgcggt       960
cctcttcctg ctgtctgttt actccctagg ccccgctggg gacctgggaa agagggaaag      1020
gcttccccgg ccagctgcgc ggcgactccg gggactccag ggcgcccctc tgcggccgac      1080
gcccggggtg cagcggccgc cggggctggg gccggcggga gtccgcggga ccctccagaa      1140
gagcggccgg cgccgtgact cagcactggg gcggagcggg gcgggaccac ccttataagg      1200
ctcggaggcc gcgaggcctt cgct gga gtt tcg ccg ccg cag tct tcg cca      1251 cca gtgagtacgc gcggcccgct ccccggggat ggggctcaga gctcccagca             1304
tggggccaac ccgcagcatc aggcccgggc tccggcagg gctcctcgcc cacctcgaga      1364
cccgggacgg gggcctaggg gacccaggac gtccccagtg ccgttagcgg ctttcagggg      1424
gcccggagcg cctcggggag ggatgggacc ccggggcgg ggagggggg caggctgcgc      1484 tcaccgcgcc ttggcatcct ccccccgggct ccagcaaact tttctttgtt cgctgcagtg      1544
ccgccctaca ccgtggtcta tttcccagtt cgaggtagga gcatgtgtct ggcagggaag      1604
ggaggcaggg gctggggctg cagcccacag cccctcgccc acccggagag atccgaaccc      1664
ccttatccct ccgtcgtgtg gcttttaccc cgggcctcct tcctgttccc cgcctctccc      1724
gccatgcctg ctccccgccc cagtgttgtg tgaaatcttc ggaggaacct gtttacctgt      1784
tccctccctg cactcctgac ccctccccgg gttgctgcga ggcggagtcg gcccggtccc      1844
cacatctcgt acttctccct ccccgcaggc cgctgcgcgg ccctgcgcat gctgctggca      1904
gatcagggcc agagctggaa ggaggaggtg gtgaccgtgg agacgtggca ggagggctca      1964
```

```
ctcaaagcct cctgcgtaag tgaccatgcc cgggcaaggg gagggggtgc tgggccttag    2024
ggggctgtga ctaggatcgg gggacgccca agctcagtgc ccctccctga gccatgcctc    2084
ccccaacagc tatacgggca gctccccaag ttccaggacg agacctcac cctgtaccag     2144
tccaatacca tcctgcgtca cctgggccgc acccttggtg agtcttgaac ctccaagtcc    2204
agggcaggca tgggcaagcc tctgcccccg gagccctttt gtttaaatca gctgccccgc    2264
agccctctgg agtggaggaa actgagaccc actgaggtta cgtagtttgc ccaaggtcaa    2324
gcctgggtgc ctgcaatcct tgccctgtgc caggctgcct cccaggtgtc aggtgagctc    2384
tgagcacctg ctgtgtggca gtctctcatc cttccacgca catcctcttc ccctcctccc    2444
aggctggggc tcacagacag cccctggtt ggcccatccc cagtgactgt gtgttgatca     2504
ggcgcccagt cacgcggcct gctccctcc acccaacccc agggctctat ggaaggacc      2564
agcaggaggc agccctggtg gacatggtga atgacggcgt ggaggacctc cgctgcaaat    2624
acatctccct catctacacc aactatgtga gcatctgcac cagggttggg cactggggc     2684
tgaacaaaga aaggggcttc ttgtgccctc accccctta cccctcaggt ggcttgggct     2744
gaccccttct tgggtcaggg tgcaggggct ggtcagctc tgggccaggg gcccaggggc     2804
ctgggacaag acacaacctg caccttatt gcctgggaca tcaaccagcc aagtaacggg     2864
tcatggggc gagtgcaagg acagagacct ccagcaactg gtggtttctg atctcctggg     2924
gtggcgaggg cttcctggag tagccagagg tggaggagga tttgtcgcca gtttctggat    2984
ggaggtgctg gcactttag ctgaggaaaa tatgcagaca cagagcacat ttgggaccct     3044
gggaccagtt cagcagaggc agcgtgtgtg cgcgtgcgtg tgcgtgtgtg tgcgtgtgtg    3104
tgtgtacgct tgcatttgtg tcgggtgggt aaggagatag agatgggcgg gcagtaggcc    3164
caggtcccga aggccttgaa cccactggtt tggagtctcc taagggcaat gggggccatt    3224
gagaagtctg aacagggctg tgtctgaatg tgaggtctag aaggatcctc cagagaagcc    3284
agctctaaag cttttgcaat catctggtga gagaacccag caaggatgga caggcagaat    3344
ggaatagaga tgagttggca gctgaagtgg acaggatttg gtactagcct ggttgtgggg    3404
agcaagcaga ggagaatctg ggactctggt gtctggcctg gggcagacgg gggtgtctca    3464
ggggctggga gggatgagag taggatgata catggtggtg tctggcagga ggcgggcaag    3524
gatgactatg tgaaggcact gcccgggcaa ctgaagcctt ttgagaccct gctgtcccag    3584
aaccagggag gcaagacctt cattgtggga gaccaggtga gcatctggcc ccatgctgtt    3644
ccttcctcgc caccctctgc ttccagatgg acacaggtgt gagccatttg tttagcaaag    3704
cagagcagac ctaggggatg ggcttaggcc ctctgccccc aattcctcca gcctgctccc    3764
gctggctgag tccctagccc ccctgccctg cagatctcct tcgctgacta caacctgctg    3824
gacttgctgc tgatccatga ggtcctagcc cctggctgcc tggatgcgtt ccccctgctc    3884
tcagcatatg tggggcgcct cagtgcccgg cccaagctca aggccttcct ggcctccct    3944
gagtacgtga acctccccat caatggcaac gggaaacagt gagggttggg gggactctga    4004
gcggaggca gagtttgcct tcctttctcc aggaccaata aaatttctaa gagagctact     4064
atgagcactg tgtttcctgg gacggggctt aggggttctc agcctcgagg tcggtgggag    4124
ggcagagcag aggactagaa aacagctcct ccagcacagt cagtggcttc ctggagccct    4184
cagcctggct gtgttactg aacctcacaa actagaagag gaagaaaaaa aagagagag     4244
agaaacaaag agaaata                                                   4261
```